United States Patent [19]
Johnson-Rabbett

[11] Patent Number: 5,392,974
[45] Date of Patent: Feb. 28, 1995

[54] MEDICAL GLOVE HOLDER

[76] Inventor: Becky L. Johnson-Rabbett, 29680 Glader Blvd., Lindstrom, Minn. 55045

[21] Appl. No.: 127,173

[22] Filed: Sep. 27, 1993

[51] Int. Cl.6 ............................................. A45F 5/00
[52] U.S. Cl. .................................... 224/253; 224/224; 224/228; 224/236; 383/906; 206/278
[58] Field of Search ............... 224/901, 235, 223, 224, 224/228, 253, 254, 226, 227, 229, 236; 206/38, 260, 234, 278, 438; 221/34, 45, 61, 62; 383/41, 47, 66, 906; 132/312

[56] References Cited

U.S. PATENT DOCUMENTS

| | | | |
|---|---|---|---|
| D. 206,983 | 2/1967 | Knight | 224/253 |
| 1,214,895 | 2/1917 | Carr | 224/228 |
| 1,290,671 | 1/1919 | Sherwood | 132/312 |
| 1,842,728 | 1/1932 | Molins | 206/254 |
| 2,510,918 | 6/1950 | Wax | 383/906 |
| 2,604,253 | 7/1952 | Turner | 206/493 |
| 2,687,159 | 8/1954 | Dobbs et al. | 150/152 |
| 2,687,835 | 8/1954 | Plonczak | 224/235 |
| 4,402,403 | 9/1983 | Focke et al. | 206/260 |
| 4,411,267 | 10/1983 | Heyman | 224/224 |
| 4,844,293 | 7/1989 | McLaughlin | 206/278 |
| 4,852,783 | 8/1989 | Bryden et al. | 224/901 |
| 4,896,805 | 1/1990 | Klaczak et al. | 224/236 |
| 4,942,992 | 7/1990 | Fischer et al. | 224/901 |
| 4,979,613 | 12/1990 | McLaughlin et al. | 224/901 |
| 5,076,431 | 12/1991 | Thompson | 206/438 |
| 5,244,136 | 9/1993 | Collaso | 224/235 |
| 5,265,785 | 11/1993 | Chudy | 206/278 |

Primary Examiner—Henry J. Recla
Assistant Examiner—Gregory M. Vidovich

[57] ABSTRACT

A glove holder particularly adapted for use with protective gloves, which is specifically designed to store a substantial supply of gloves particularly for emergency medical personnel and is adapted to be carried by the belt of the user to provide a readily available supply of medical gloves, and which is provided with a dispensing opening, specifically designed to dispense one glove at a time.

3 Claims, 1 Drawing Sheet

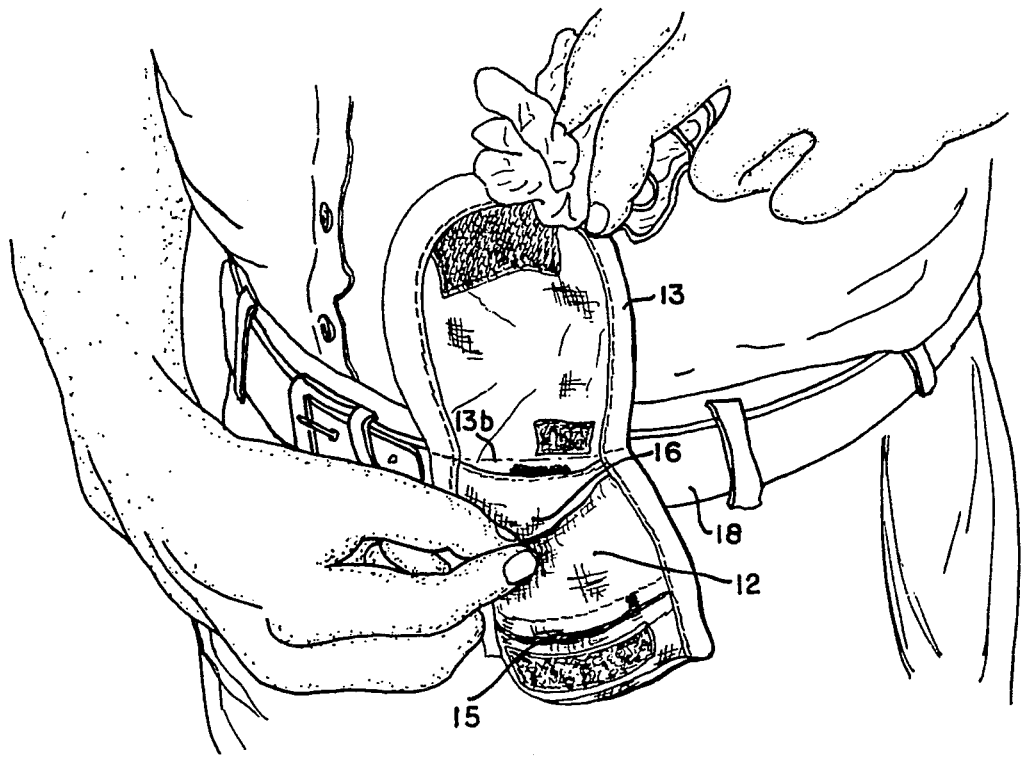
FIG. 1
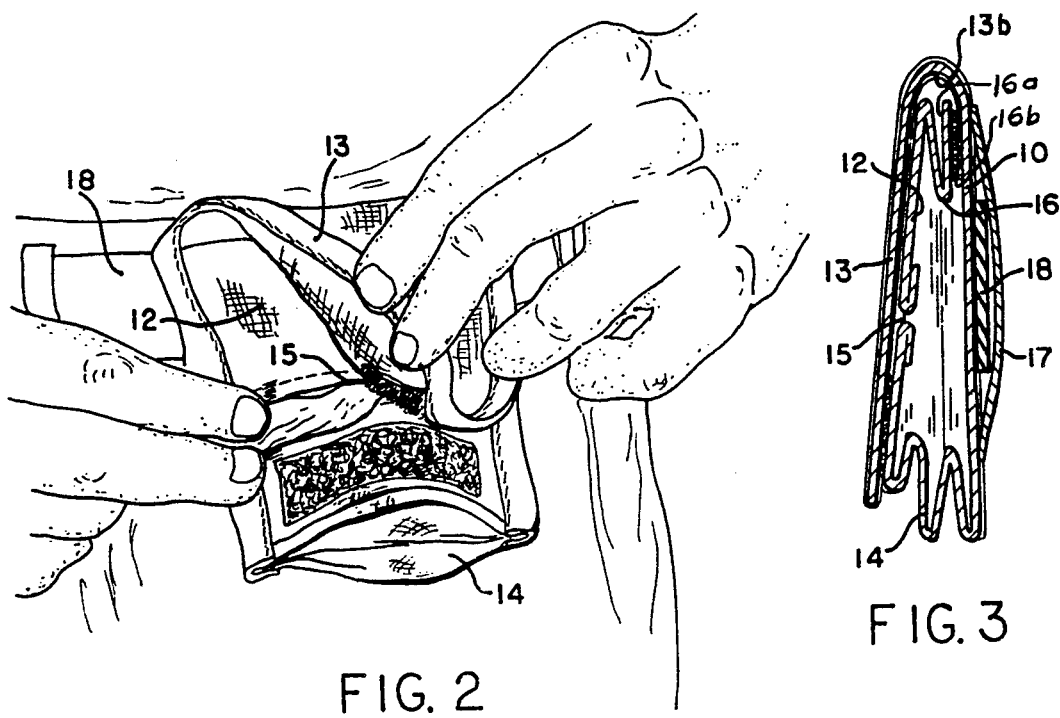
FIG. 2
FIG. 3

MEDICAL GLOVE HOLDER

BACKGROUND OF THE INVENTION

In recent years it has become imperative that medical personnel wear protective gloves to prevent contact with the blood and other body fluids from a patient, and therefore it is important to provide a readily accessible supply of protective gloves. This can be accomplished most readily by attaching a glove-holding pouch to the belt of the individual rendering the emergency care to facilitate access to a substantial supply of such gloves. The particular design of the pouch embodying this invention materially increases not only the capacity of the pouch, but also greatly facilitates the necessary one-glove-at-a-time dispensing of the gloves from the pouch pocket.

SUMMARY OF THE INVENTION

This invention constitutes a glove storage pouch for attachment to the wearer's belt, and which will hold between three and six pairs of protective plastic gloves for emergency use by emergency personnel who must treat bleeding wounds and injuries in the field.

The present invention provides a pouch which is capable of being attached to the belt for storing and dispensing protective gloves. It is important that the gloves be quickly and easily accessible, preferably with one hand of the individual user. The holder/dispenser pouch is specifically adapted to be attached to the belt of the wearer.

The pouch has an access dispenser slit formed in the front panel thereof which permits the gloves to be pulled out of the pouch, one glove at a time, when the gloves are to be used. The dispenser slit is substantially shorter than the width of the pouch, and the front panel is provided with a gusset fold immediately above the front slit to materially assist in providing a one-at-a-time dispensing operation of the gloves by the user. A retaining loop is provided on the back of the pouch, through which the wearer's belt passes. This leaves a maximum area of Velcro attachment surface on the belt exposed for attachment of other emergency items required by personnel.

DETAILED DESCRIPTION OF THE DRAWINGS

FIG. 1 is a perspective view of the glove holder mounted on a wearer's belt with the front closure flap in a filling position;

FIG. 2 is a similar view, showing the flap in partially closed position; and

FIG. 3 is a vertical section taken along the line 3—3 of FIG. 1.

DETAILED DESCRIPTION OF THE PREFERRED EMBODIMENT

Applicant's pouch made from flexible sheet material and includes a back panel 10 and a front panel 12 and a closure flap 13 which form a storage pocket therebetween. A closure flap 13 is attached to the top of the back panel 10 and overlaps the front panel 12. Suitable anchor means, such as the pair of mating Velcro patches 13a, are provided to hold the closure flap 13 in overlapped closed position. The closure flap hinges along a fold line 13b at the top of the back panel, and a gusset fold 14 joins the bottom edges of the back panel 10 and the front panel 12.

A restricted discharge slit 15 is provided in an intermediate portion of front panel 12 to provide access to the storage pocket formed between the back panel 10 and the front panel 12. The ends of the restricted discharge slit 15 are defined by suitable reinforcing, such as the stitching 15a, best shown in FIG. 1. An upper gusset fold 16 is provided in the front panel 12 above the slit 15 and forms a rear edge portion 16a which has a suitable releasable attachment to upper portion of the back panel 10 such as the pair of adhesion patches 16b as best shown in FIG. 3. The adhesion patches permit the rear edge portion 16a above the gusset fold 16 to form an access opening through which a supply of gloves may be readily inserted into the pouch.

In the form shown, the back panel 10 is integrally connected with the closure flap 13 along a fold line 13b. The top edge of the front panel 12 provides an access opening to the storage compartment through which the gloves may be readily stuffed as shown in FIG. 1. Suitable means are provided for attaching the pouch to the belt of the user such as a hook or loop 17 provided on the back side of the back panel 10 to attach the pouch at a convenient location on the wearer's belt 18.

It should be pointed out that the gusset fold 14 substantially increases the capacity of the pouch while the restricted discharge slit 15 with the gusset fold 16 disposed above the slit to facilitate access to the gloves and permit one-at-a-time dispensing through the slit while permitting each glove to be quickly pulled out of the storage pocket.

What is claimed is:

1. A medical glove holder pouch made from flexible sheet material adapted to be mounted for quick access at the waist of a user, said pouch comprising a rear panel and a front panel, each panel having side and bottom edges joined together at the sides and bottom edges thereof and defining a storage compartment therebetween sized to accommodate a plurality of gloves therein, the front and back panels defining a loading opening at a top edge of the panels having a dispensing opening disposed below the top edge of the front panel in upwardly spaced relation from the bottom edge of the front panel and communicating with the compartment to afford access to the compartment, said dispensing opening extending only partially across the front panel and being shorter than the width of the front panel for restricting the passage of the gloves from the storage compartment and thereby facilitate one-at-a-time release of the gloves from the compartment, belt attachment means located on the rear panel of the pouch for attaching the pouch to a belt of the user, and a closure flap connected at the top edge of the rear panel and adapted to overly the dispensing opening in the front panel to normally enclose the dispensing and loading openings, said flap having releasable connection means for releasable connection to the front panel but being releasable into an open position to permit access to the dispensing and loading openings.

2. The structure set forth in claim 1 and an expansion fold joining together said bottom edges of said panel to provide expansion of the compartment and increase the storage capacity thereof.

3. The structure set forth in claim 1 and a gusset formed on the inside of the front panel above the dispensing opening to facilitate access to the storage compartment through said loading opening thereby allowing said plurality of gloves to be inserted into the compartment through the loading opening.

* * * * *